United States Patent [19]

Hirai et al.

[11] 4,309,433
[45] Jan. 5, 1982

[54] PYRIDINECARBONAMIDO-OXY OR THIO LOWERALKYL-1-(DILOWERALKYLAMINOLOWERALKYL)BENZENE AND DERIVATIVES THEREOF, COMPOSITIONS CONTAINING SAME AND METHOD OF USING SAME

[75] Inventors: Kentaro Hirai, Kyoto; Teruyuki Ishiba, Takatsuki; Shigeru Matsutani, Sakai; Itsuo Makino, Kobe; Toshio Fujishita, Neyagawa; Masami Doteuchi, Hirakata; Koichi Otani, Kawachinagano, all of Japan

[73] Assignee: Shionogi & Co., Ltd., Osaka, Japan

[21] Appl. No.: 164,016

[22] Filed: Jun. 30, 1980

[30] Foreign Application Priority Data

Jul. 3, 1979 [JP] Japan .................................. 54-84801

[51] Int. Cl.³ .................. A61K 31/455; C07D 401/10; C07D 213/56
[52] U.S. Cl. .................................... 424/266; 546/281; 546/316; 546/323; 546/208; 546/330; 260/326.35; 260/326.36; 260/347.2; 260/347.3; 260/347.7; 548/240; 548/269; 548/342; 549/13; 549/70; 549/75; 564/161; 564/169; 564/189; 564/190
[58] Field of Search .................. 546/281, 316, 323; 424/266

[56] References Cited

U.S. PATENT DOCUMENTS 4,255,582 3/1981 Sollman ............................... 546/323

Primary Examiner—Alan L. Rotman
Attorney, Agent, or Firm—Wenderoth, Lind & Ponack

[57] ABSTRACT

An aminoalkylbenzene derivative of the formula:

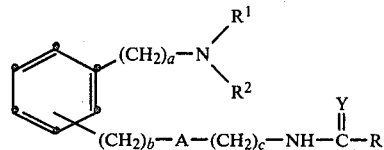

[wherein
A is oxygen or sulfur;
Y is oxo, thioxo, or cyanoimino;
a is an integer of 1 to 3;
b is an integer of 0 to 3;
c is an integer of 1 to 4;
$R^1$ is alkyl;
$R^2$ is hydrogen or alkyl; or
$R^1$ and $R^2$ taken together represent pyrrolidinyl;
R is hydrogen, cycloalkyl, trihaloalkyl, alkoxy, dialkylamino, aryl, aroyl, heterocyclic group, or a group of the formula:

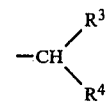

(wherein
$R^3$ is hydrogen, halogen, amino, alkyl, alkylamino, dialkylamino, alkylthio, or aryloxy;
$R^4$ is hydrogen, alkyl, alkenyl, aryl, or heterocyclic group; or
$R^3$ and $R^4$ taken together represent alkylidene or aralkylidene;
with the proviso that the above aryl, aroyl, and heterocyclic group can be substituted by 1 to 3 substituents] and its pharmaceutically acceptable acid addition salts being useful as histamine $H_2$ blockers, especially peptic ulcer remedies, are provided via several routes.

7 Claims, No Drawings

PYRIDINECARBONAMIDO-OXY OR THIO LOWERALKYL-1-(DILOWERALKYLAMINOLOWERALKYL)BENZENE AND DERIVATIVES THEREOF, COMPOSITIONS CONTAINING SAME AND METHOD OF USING SAME

I. SUMMARY OF THE INVENTION

This invention relates to novel aminolkylbenzene derivatives useful as histamine $H_2$ antagonists.

Division of histamine receptors (H-receptors) into two subclasses $H_1$- and $H_2$- receptors has recently been proposed by Ash and Schild (Brit. J. Pharmacol. Chemother., 27(1966), 427) and Black et al. (Nature, 236(1972), 385). Thus the stimulation of bronchial and gastrointestinal smooth muscle is mediated by $H_1$-receptor; this effect can be inhibited by known antihistamine agents such as mepyramine. Stimulations for the secretion of gastric juice, ventricular systole and auricular pulsation are mediated by $H_2$-receptors; these effects are not inhibited by mepyramine but $H_2$-antagonists such as metiamide and cimetidine [G. J. Durant, C. R. Ganellin et al., J. Med. Chem., 20(1977), 901].

As the result of various investigations for finding such compounds binding to histamine $H_2$-receptor which can exhibit an effective activity in peptic ulcer remedy, the present inventors have found that certain novel aminoalkylbenzene derivatives exhibit excellent histamine $H_2$ antagonism. Thus the present invention has been established on the basis of this finding.

Accordingly, this invention is directed to the compounds of the formula:

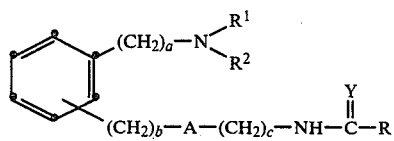

(I)

[wherein
A is oxygen or sulfur;
Y is oxo, thioxo, or cyanoimino;
a is an integer of 1 to 3;
b is an integer of 0 to 3;
c is an integer of 1 to 4;
$R^1$ is $C_1$ to $C_5$ alkyl;
$R^2$ is hydrogen or $C_1$ to $C_5$ alkyl; or
$R^1$ and $R^2$ taken together represent pyrrolidinyl;
R is hydrogen, $C_3$ to $C_6$ cycloalkyl, $C_1$ to $C_5$ trihaloalkyl; $C_1$ to $C_5$ alkoxy, $C_2$ to $C_6$ dialkylamino, $C_6$ to $C_{10}$ aryl, $C_7$ to $C_{11}$ aroyl, heterocyclic group selected from the group consisting of thienyl, furyl, pyrrolidinyl, isoxazolyl, imidazolyl, triazolyl, thiopyranyl, pyridyl, piperidyl and 4,5,6,7-tetrahydroisoxazolo [4,5-c] pyridyl, or a group of the formula:

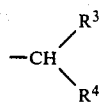

(wherein $R^3$ is hydrogen, halogen, amino, $C_1$ to $C_5$ alkyl, $C_1$ to $C_5$ alkylamino, $C_2$ to $C_6$ dialkylamino, $C_1$ to $C_5$ alkylthio, or $C_6$ to $C_{10}$ aryloxy;
$R^4$ is hydrogen, $C_1$ to $C_5$ alkyl, $C_3$ to $C_5$ alkenyl, $C_6$ to $C_{10}$ aryl, or heterocyclic group selected from the group consisting of tetrazolyl, oxadiazolyl, piperidyl, and morpholinyl; or
$R^3$ and $R^4$ taken together represent $C_1$ to $C_5$ alkylidene or $C_7$ to $C_{12}$ aralkylidene)

with the proviso that the above aryl and aroyl can be substituted by 1 to 3 substituents selected from the group consisting of hydroxy, halogen, amino, nitro, cyano, carboxy, carbamoyl, sulfamoyl, $C_1$ to $C_5$ alkanesulfonyl, $C_1$ to $C_5$ alkanesulfonamido, benzoyl, $C_1$ to $C_5$ alkyl, $C_1$ to $C_5$ alkoxy, $C_2$ to $C_6$ alkoxycarbonyl, $C_2$ to $C_6$ dialkylamino, $C_1$ to $C_5$ alkanoylamino, and tetrazolyl; and the above heterocyclic group can be substituted by 1 to 3 substituents selected from the group consisting of halogen, nitro, oxo, phenyl, $C_1$ to $C_5$ alkyl, and $C_1$ to $C_5$ alkanoyl]and its pharmaceutically acceptable acid addition salts.

II. DETAILED EXPLANATION

In the above general formula (I), $C_1$ to $C_5$ alkyl means methyl, ethyl, propyl, butyl, isobutyl, s-butyl, t-butyl, pentyl, and the like, preferably methyl, ethyl, and propyl. $C_1$ to $C_5$ Alkylthio means methylthio, ethylthio, propylthio, butylthio, pentylthio, and the like, preferably methylthio. $C_1$ to $C_5$ Trihaloalkyl means trifluoromethyl, trifluoroethyl, dibromochlorobutyl, and the like, preferably trifluoromethyl. $C_3$ to $C_6$ Cycloalkyl means cyclopropyl, cyclobutyl, cyclopentyl, cyclohexyl, and the like, preferably cyclopropyl and cyclohexyl. $C_3$ to $C_5$ Alkenyl means allyl, isopropenyl, butenyl, and pentenyl, preferably allyl. $C_1$ to $C_5$ Alkoxy means methoxy, ethoxy, propoxy, isopropoxy, butoxy, isobutoxy, s-butoxy, t-butoxy, pentyloxy, and the like, preferably methoxy and ethoxy. $C_2$ to $C_6$ Alkoxycarbonyl means methoxycarbonyl, ethoxycarbonyl, propoxycarbonyl, butoxycarbonyl, pentyloxycarbonyl, and the like, preferably methoxycarbonyl. $C_1$ to $C_5$ Alkanoyl means formyl, acetyl, propionyl, butyryl, isobutyryl, valeryl, isovaleryl, pivaloyl, and the like, preferably acetyl. $C_1$ to $C_5$ Alkanoylamino means formylamino, acetylamino, propionylamino, butyrylamino, isobutyrylamino, valerylamino, isovalerylamino, pivaloylamino, and the like, preferably acetylamino. $C_1$ to $C_5$ Alkylamino means methylamino, ethylamino, propylamino, isopropylamino, butylamino, isobutylamino, pentylamino, and the like. $C_2$ to $C_6$ Dialkylamino means dimethylamino, diethylamino, dipropylamino, methylethylamino, methylbutylamino, and the like, preferably dimethylamino and diethylamino. $C_1$ to $C_5$ Alkanesulfonyl means methanesulfonyl, ethanesulfonyl, propanesulfonyl, butanesulfonyl, pentanesulfonyl, and the like. $C_1$ to $C_5$ alkanesulfonamido means methanesulfonamido, ethanesulfonamido, propanesulfonamido, butanesulfonamido, pentanesulfonamido, and the like. $C_1$ to $C_5$ Alkylidene means methylidene, ethylidene, propylidene, isopropylidene, butylidene, pentylidene, and the like, preferably methylidene and isopropylidene. $C_7$ to $C_{12}$ Aralkylidene means benzylidene and naphthylmethylidene. $C_6$ to $C_{10}$ Aryl means phenyl and naphthyl. $C_6$ to $C_{10}$ Aryloxy means phenoxy and naphthyloxy. $C_7$ to $C_{11}$ Aroyl means benzoyl and naphthoyl. Halogen means fluoro, chloro, bromo, and iodo.

Compounds (I) can be easily converted to the corresponding pharmaceutically acceptable acid addition salts, which are included within the scope of this invention. Representative acids which can form the pharmaceutically acceptable salts are inorganic acids such as hydrochloric acid, hydrobromic acid, hydroiodic acid, sulfuric acid, nitric acid, phosphoric acid, and the like and organic acids such as acetic acid, oxalic acid, fumaric acid, malic acid, tartaric acid, citric acid, maleic acid, mandelic acid, succinic acid, and the like.

III. PREPARATION

Compounds (I) may be easily prepared according to any one of the following manners:

Reaction Scheme 1

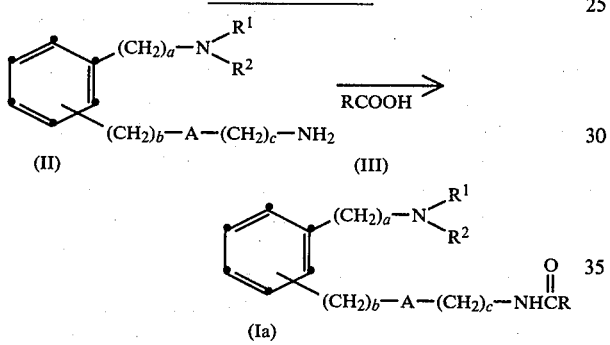

(wherein each symbol has the same meaning as given earlier.)

This process may be carried out by reacting Compound (II) with carboxylic acid (III) or reactive derivatives thereof (e.g. acid halide, ester residue, mixed acid anhydride residue). This reaction may be carried out in an inert solvent (e.g. dimethylformamide, methylene chloride, acetonitrile, tetrahydrofuran) at room temperature or under cooling or heating up to the boiling point of the solvent used, if necessary, in the presence of a condensing agent (e.g. DCC) and a base (e.g. triethylamine, pyridine).

Reaction Scheme 2

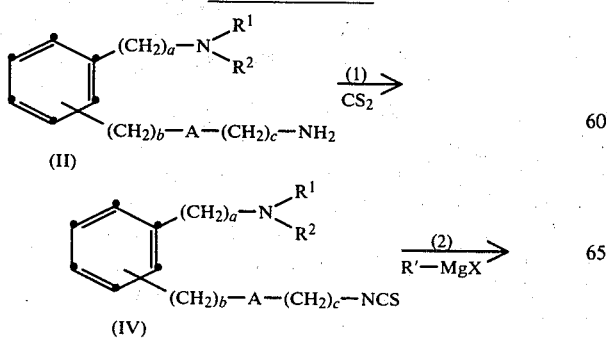

-continued
Reaction Scheme 2

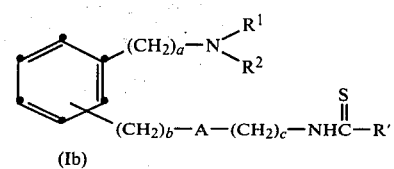

(wherein R' is alkyl or aryl; other symbols have the same meaning as given earlier.)

(1) Compound (II) is reacted with carbon disulfide in an inert solvent to give the corresponding dithiocarbamate, and the latter is subjected to isothiocyanate formation to give Compound (IV). Isothiocyanate formation may be effected by treatment of dithiocarbamate with metal salts such as mercury (II) chloride, silver nitrate, ferric chloride, or the like and then by heating with water, or by treatment of dithiocarbamate with 2-bromo-3-ethyl-4-phenylthiazolium fluoroborate and triethylamine.

(2) This reaction may be carried out by reacting isothiocyanate (IV) with Grignard reagent in an inert solvent (e.g. ether, tetrahydrofuran) at room temperature or under cooling or heating up to the boiling point of the solvent used.

Reaction Scheme 3

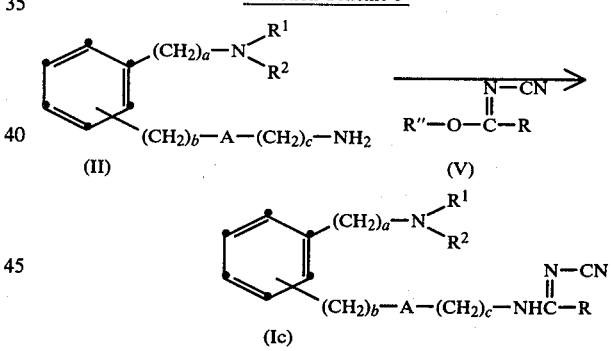

(wherein R'' is alkyl; and other symbols have the same meaning as given earlier.)

This reaction may be carried out by reacting Compound (II) with Compound (V) in a suitable solvent at room temperature or under gentle warming (e.g. at the boiling point of the solvent). Representative solvents are methanol, ethanol, dimethylsulfoxide, dimethylformamide, benzene, toluene, and the like.

Reaction Scheme 4

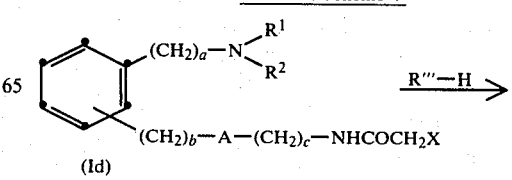

-continued
Reaction Scheme 4

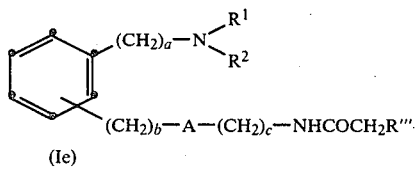

(Ie)

(wherein
X is halogen;
R'''is amino, alkylamino, dialkylamino, alkylthio, or aryloxy;
other symbols have the same meaning as given earlier.)

This reaction may be carried out in the presence of a base (e.g. triethylamine) at room temperature or under heating up to the boiling point of the solvent used.

Compound (Id) may be prepared according to Reaction Scheme 1.

Reaction Scheme 5

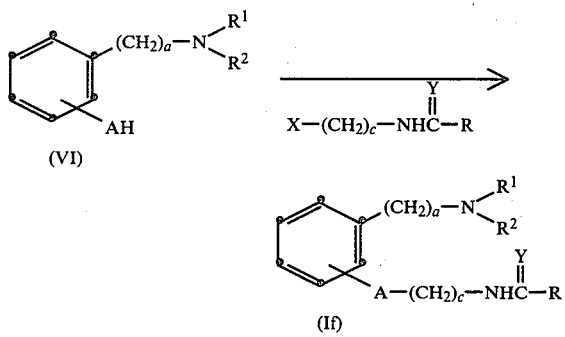

(wherein each symbol has the same meaning as given earlier.)

This reaction is etherification and may be carried out in the presence of a base (e.g. sodium hydride, sodium ethoxide, potassium amide, triethylamine) in an inert solvent (e.g. dimethylformamide, hexamethylphosphoric triamide (HMPT), tetrahydrofuran, dimethylsulfoxide) at room temperature or under cooling or heating up to the boiling point of the solvent used.

IV. EFFECT

Compounds (I) and the pharmaceutically acceptable salts thereof prepared in this invention are useful as peptic ulcer remedies or histamine $H_2$ receptor antagonists.

(1) Blocking Action on Histamine $H_2$ Receptor in vitro

Histamine $H_2$ receptor blocking activity of the compound was determined by obtaining the dose-response relationship of the positive chronotropic effect of histamine in spontaneously beating atria of guinea pig in vitro, in the absence and in the presence of a test compound. The activity was shown in Table 1 as $pA_2$ value for each compound, defined as a negative logarithm of the concentration of the compound required to shift the dose-response of histamine to the right by 2-fold. E. J. Ariens. Molecular Pharmacology, vol. 1, 153–156 (1964), Academic Press, New York).

TABLE 1

$$\text{aryl-}CH_2N\begin{matrix}R^1\\R^2\end{matrix} \cdot n(COOH)_2$$

$$O-(CH_2)_3-NHCOR$$

| Comp. No. | $-N\begin{matrix}R^1\\R^2\end{matrix}$ | R | n | $pA_2$ |
|---|---|---|---|---|
| 1 | (azetidinyl) | (pyridyl) | 2¼ | 6.89 |
| 2 | " | —Ph | 1 | 6.72 |
| 3 | " | (thienyl) | 1 | 6.86 |
| 4 | " | —$CH_3$ | 1 | 6.71 |
| 5 | " | (phenyl-COOCH₃) | 1 | 7.09 |
| 6 | " | H | 1 | 6.77 |
| 7 | " | (phenyl-$NO_2$) | 1 | 7.00 |
| 8 | " | (isoxazolyl-Ph) | 1 | 6.73 |
| 9 | Cimetidine | | | 6.63 |

(Note)
Ph = phenyl (2) Inhibitory action against the gastric acid secretion

Inhibitory action of a test compound against the gastric acid secretion induced by histamine was determined according to the method of Ghosh and Schild (M. N. Ghosh and H. O. Schild: Br. J. Pharmacol. 13, 54, 1958) with some modifications. Male Donryu rats weighing 200±10 g were deprived of food for 24 hr prior to the experiments, with water ad lib. Under the anesthesia with 1.2 g/kg of subcutaneous urethane, trachea and cervical vein were cannulated. With midline opening, the duodenum immediately below the junction with pylorus was incised and after the stomach was flashed with saline for several times, the polyethylene tube was inserted into the pylorus through the incision, and ligated with surrounding tissues keeping the blood vessels intact. The polyvinyl tube was inserted into the mouth up to the forestomach through the esophagus and ligated at the cervical level. Saline solution kept at 35° C. was perfused through the polyvinyl tube at the rate of 1 ml/min, and the perfusate was collected through the polyethylene tube of the pylorus. The perfusate was collected for 30 min and was titrated by 0.01 N NaOH with phenolphthalein as an indicator to obtain a total acid output(mEq). Subsequently, the perfusate was collected for every 30 min. After the acid output became constant, the stomach was perfused for further 60 min. After that, in the control group, 0.1 ml of saline per 100 g of body weight was intravenously injected, 10 min later 5 mg/kg of histamine dihydrochloride was injected intravenously. The perfusate for 60 min after histamine injection was collected and determined the acidity. The amount of acid output during 60 min after histamine injection subtracted that for 60 min before histamine was regarded as the acid output response to histamine. In the test groups, following the injection of three compounds (A), (B) and (C) instead of saline, 5 mg/kg of histamine dihydrochloride was injected and acid output was determined. Decreased ratio of the acid output to the control was calculated as the response to the test compound. From the dose-response relationship for each compound, $ED_{50}$, a dose to inhibit 50% of acid output of the control was calculated.

TABLE 2

| Compound | R | n | $ED_{50}$ (mg/kg) |
|---|---|---|---|
| A | ![pyridine-CO] | 2¼ | 1.25 |
| B | —COCH$_3$ | 1 | 1.65 |
| C | —CHO | 1 | 0.84 |

(Structure above table: benzene with CH$_2$—N(ring), n(COOH)$_2$, O—(CH$_2$)$_3$—NHR)

(3) Acute Toxicity

To test the acute toxicity of each compound (A), (B) and (C), $LD_{50}$ was determined using SLC-ddY male mice of aging 4 weeks. Results are shown in Table 3.

TABLE 3

| Compound | R | n | $LD_{50}$ value (mg/kg) p.o. |
|---|---|---|---|
| A | ![pyridine-CO] | 2¼ | >1000 |
| B | —COCH$_3$ | 1 | >1000 |
| C | —CHO | 1 | >1000 |

V. HOW TO USE

Compounds (I) or pharmaceutically acceptable salts thereof may be administered in enteral application or parenteral applications such as subcutaneous, intramuscular and intravenous injection. Compounds (I) or pharmaceutically acceptable salts thereof may be found solely or in admixture with additives such as diluents, carriers, preservatives, stabilizers, or flavoring agents to oral dosage form such as tablets, capsules and elixirs or parenteral dosage form such as sterile solution and suspension. The formulations may be dispensed in a conventional manner. For example, Compounds (I) may be administered at a dose of 1 to 40 mg/kg per day, preferably 1 to 15 mg/kg per day in single or multiple divisions to human adults.

The following examples are provided to further illustrate this invention.

EXAMPLE 1

Preparation of 3-(2-propionamidoethyl)thiomethyl-1-dimethylaminomethylbenzene

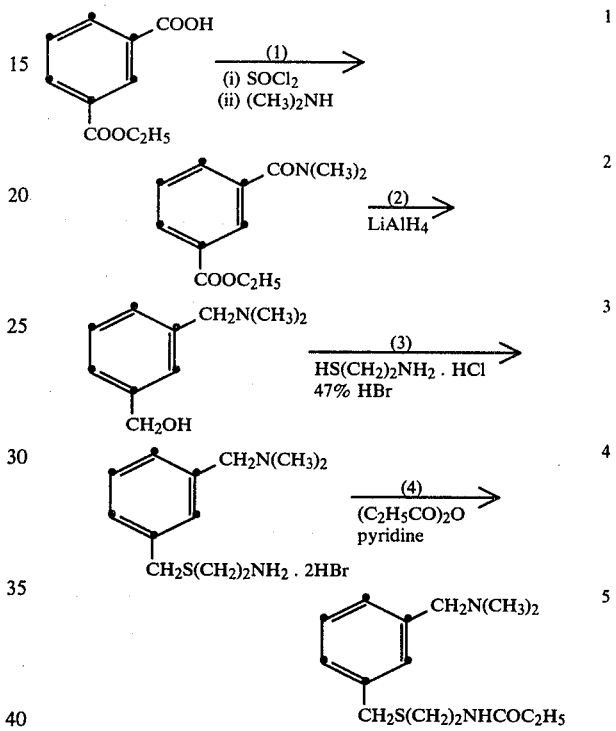

(1) A mixture of Compound 1 (2.7 g; 15 mmoles) and thionyl chloride (2.7 g; 22.5 mmoles) is refluxed under heating for 30 minutes and concentrated under reduced pressure. The residue is mixed with benzene and evaporated under reduced pressure again to give an oily residue. To a solution of the residue in chloroform (20 ml) is added a mixture of dimethylamine and water (50:50)(about 6 ml) under ice-cooling with stirring, and the mixture is stirred at the same temperature for 10 minutes and at room temperature for 2 hours. Chloroform layer is separated, dried over anhydrous Glauber's salt, and concentrated under reduced pressure to give Compound 2 (1.95 g).

Yield 65%

(2) To a suspension of lithium aluminium hydride (2.1 g; 55.7 mmoles) in dry tetrahydrofuran (50 ml) is added a solution of Compound 2 (1.95 g; 9.3 mmoles) in dry tetrahydrofuran (20 ml) at temperature below 20° C., and the mixture is stirred at the same temperature for 1 hour and at room temperature for 3 hours, mixed with ethyl acetate (20 ml) at temperature below 20° C., diluted with water (20 ml), and then stirred at room temperature for 30 minutes. The insoluble materials are filtered off and the filtrate is evaporated under reduced pressure. The residue is mixed with water and extracted with methylene chloride. The methylene chloride layer is washed with water, dried over anhydrous Glauber's salt and concentrated under reduced pressure to give Compound 3 ( 1.2 g).

Yield 78.4%

NMR: $\delta^{CDCl_3}$ 2.22s(6H, CH$_3$x2), 3.42s(2H, CH$_2$N—), 4.67s(2H, C$\underline{H}_2$O)

(3) A solution of Compound 3 (1.2 g; 7.26 mmoles) and 2-mercaptoethylamine hydrochloride (0.83 g; 7.26 mmoles) in 47% aqueous hydrogen bromide (10 ml) is refluxed for 4 hours and concentrated under reduced pressure. The residue is mixed with ethanol and evaporated under reduced pressure. The resulting crystalline residue is washed with ethanol to give Compound 4 (2.4 g).

Yield 92.3%

(4) To a solution of Compound 4 (0.76 g; 2 mmoles) in dry pyridine (10 ml) is added propionic anhydride (0.273 g; 2.1 mmoles) under ice-cooling with stirring, and the mixture is allowed to stand at room temperature overnight and concentrated under reduced pressure. The residue is mixed with a mixture of sodium hydrogencarbonate and saturated brine and extracted with chloroform. The chloroform layer is washed with water, dried, and concentrated under reduced pressure to give objective Compound 5 (0.400 g) as an oily product.

Yield 71.4%

NMR: $\delta^{CDCl_3}$ 1.13t(3H, J=7 Hz, CH$_3$), 2.03s(6H, CH$_3$x2), 3.42s(2H, N—CH$_2$), 3.55s(2H, S—CH$_2$), 5.83 (1H, NH).

The oily product obtained is treated with oxalic acid/ethanol and recrystallized from ethanol to give the oxalate of Compound 5 as colorless needles.

mp. 143°~146° C.

IR: $\nu^{Nujol}$ 3260, 2700, 1720, 1640 cm$^{-1}$.

Elemental Analysis (for C$_{15}$H$_{24}$N$_2$OS.(COOH)$_2$): Calcd (%): C, 55.12; H, 7.07; N, 7.56; O, 21.59. Found (%): C, 55.21; H, 7.10; N, 7.58; O, 21.37.

EXAMPLE 2

Preparation of 3-(2-acrylamidoethyl)thiomethyl-1-dimethylaminomethylbenzene

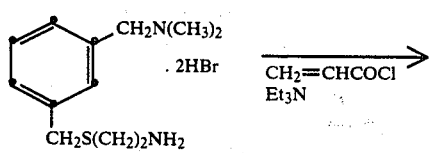

To a suspension of Compound 4 prepared in Example 1-(3) (1.38 g; 3.63 mmoles) in dimethylformamide (5 ml) are added triethylamine (0.886 g; 8.77 mmoles) and acryloyl chloride (0.559 g; 6.2 mmoles) under ice-cooling with stirring, and the mixture is allowed to stand at room temperature overnight. The reaction mixture is mixed with water (20 ml) and extracted with ethyl acetate. The ethyl acetate layer is washed with water, dried, and concentrated under reduced pressure to give objective Compound 6 (0.480 g) as an oily product.

Yield 43.7%

NMR: $\delta^{CDCl_3}$ 2.15s(6H, CH$_3$x2), 3.33s(2H, NCH$_2$), 3.63s(2H, SCH$_2$), 5.40-6.40m (CH=CH$_2$)

IR: $\nu^{film}$ 1655, 1620 cm$^{-1}$.

The above oily residue is treated with oxalic acid/ethanol and recrystallized from ethanol-ether to give the oxalate of Compound 6 as a pure product.

mp. 115°~117° C. (dec.)

Elemental Analysis (for C$_{15}$H$_{22}$N$_2$OS.(COOH)$_2$): Calcd (%): C, 55.42; H, 6.57; N, 7.60. Found (%): C, 54.91; H, 6.56; N, 7.43.

EXAMPLES 3 TO 11

Compounds shown in Table 4 are prepared from Compound 4 and the acyl chloride in the same manner as in Example 2.

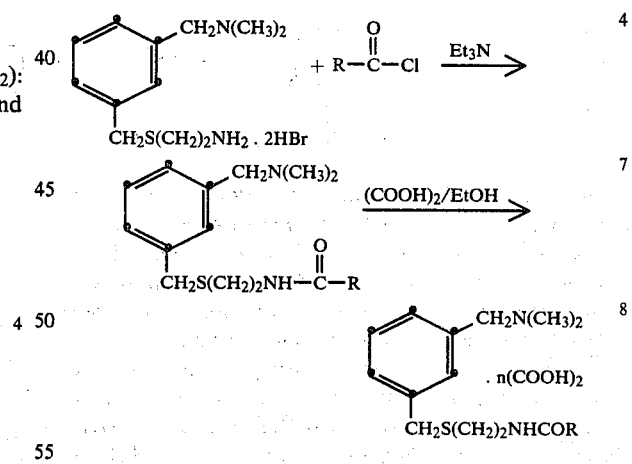

TABLE 4

| Ex. No. | R | Compound 7 NMR:$\delta^{CDCl_3}$ | Compound 8 n | mp (°C.) |
|---|---|---|---|---|
| 3 | —OC$_2$H$_5$ | 4.12q(J = 7Hz,CH$_2$), 3.73s(2H,SCH$_2$), 3.53s(2H,NCH$_2$), 2.43s(6H,CH$_3$ × 2), 1.08t(J = 7Hz,CH$_3$). | 1 | 123 ~ 125(dec.) |
| 4 | —CH$_2$Ph | 4.13(2H,PhCH$_2$CO), 3.63(2H,PhCH$_2$S), 3.53(2H,PhCH$_2$N), 2.63(6H,CH$_3$). | 1 | 105 ~ 110(dec.) |
| 5 | —CH=CHPh | 6.60d(J = 16Hz,CH), 4.12s(2H,SCH$_2$), 3.70s(2H,NCH$_2$), 2.70s(6H,CH$_3$ × 2). | 1 | 156 ~ 158 |

TABLE 4-continued

| Ex. No. | R | Compound 7 NMR:δ$^{CDCl_3}$ | Compound 8 n | mp (°C.) |
|---|---|---|---|---|
| 6 | ![3-Cl-phenyl] | 6.67b(1H,NH), 3.75s(2H,SCH$_2$), 3.38s(2H,NCH$_2$), 2.18s(6H,CH$_3$ × 2). | 1 | 98 ~ 100(dec.) (¼ H$_2$O) |
| 7 | ![2-Cl-phenyl] | 6.67b(1H,NH), 3.75s(2H,SCH$_2$), 3.42s(2H,NCH$_2$), 2.22s(6H,CH$_3$ × 2). | 1 | 152 ~ 155 (¼ H$_2$O) |
| 8 | ![3-OCH3-phenyl] | 3.97s(3H,OCH$_3$), 3.77s(2H,SCH$_2$), 3.40s(2H,NCH$_2$), 2.23s(6H,CH$_3$ × 2). | 1 | 108 ~ 110(dec.) |
| 9 | ![4-OCH3-phenyl] | 4.00s(2H,SCH$_2$), 3.83s(3H,OCH$_3$), 3.72s(2H,NCH$_2$), 2.63s(6H,CH$_3$ × 2). | 1 | 143 ~ 145(dec.) |
| 10 | ![thiophene] | 6.50b(1H,NH), 3.75s(2H,SCH$_2$), 3.42s(2H,NCH$_2$), 2.23s(6H,CH$_3$ × 2). | 1 | 126 ~ 128(dec.) |
| 11 | ![pyridine] | 3.75s(2H,SCH$_2$), 3.60s(2H,NCH$_2$), 2.35s(6H,CH$_3$ × 2). | 2½ | 169 ~ 172(dec.) |

EXAMPLE 12

Preparation of 3-[3-(phenoxyacetamido)propoxy]-1-(1-pyrrolidinylmethyl)benzene

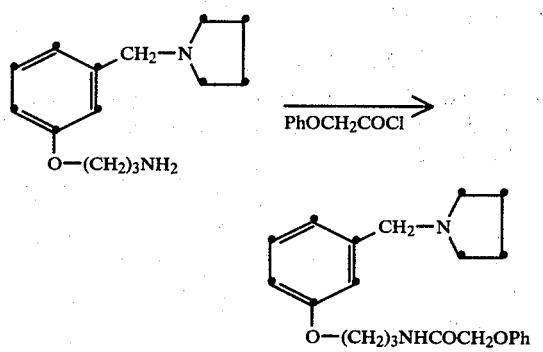

To a solution of Compound 9 (0.234 g; 1 mmole) in dry pyridine (2 ml) is slowly added phenoxyacetyl chloride (0.18 g; 1.1 mmoles) at −5° C. with stirring, and the resultant mixture is stirred at −5° C. for 1 hour and at room temperature overnight and concentrated under reduced pressure. The residue is mixed with icy water and aqueous sodium hydrogencarbonate and then extracted with chloroform. The extract is washed with water, dried over anhydrous sodium sulfate, filtered, and concentrated. The residue is chromatographed on silica gel and eluted with methanol to give Compound 10 (0.291 g) as an oily product.

Yield: 76%

NMR: δ$^{CDCl_3}$ 3.57s(2H, Ph—C$\underline{H_2}$—N), 4.50s(2H, NHCOC$\underline{H_2}$—O).

IR: ν$^{film}$ 3400, 3300, 1660, 1600, 1530 cm$^{-1}$.

Monooxalate (recrystallized from ethanol-ether) mp. 133° to 134° C.

Elemental Analysis (for C$_{22}$H$_{28}$O$_3$N$_2$.(COOH)$_2$): Calcd (%): C, 62.87; H, 6.60; N, 6.11. Found (%): C, 62.92; H, 6.62; N, 6.14.

EXAMPLES 13 TO 37

Compounds shown in Table 5 are prepared from Compound 9 and acyl chloride in the same manner as in Example 12.

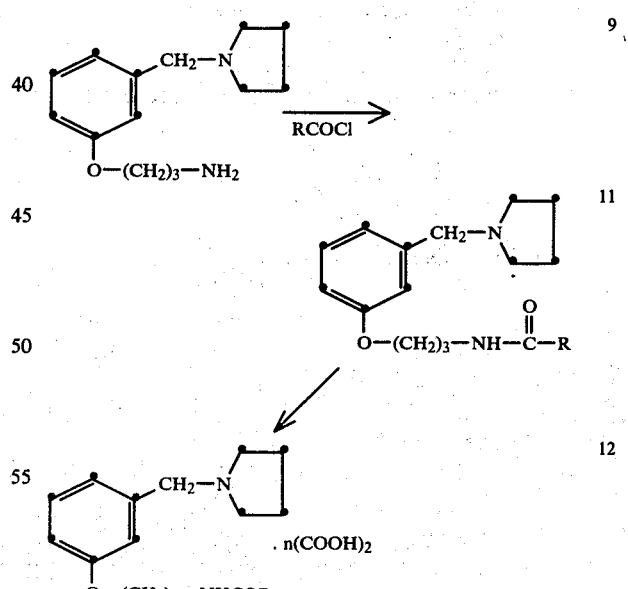

TABLE 5

| Ex. No. | R | Compound 11 NMR:δ$^{CDCl_3}$ | Compound 12 n | mp (°C.) |
|---|---|---|---|---|
| 13 | ![cyclopropyl] | 3.62s(2H, PhC$\underline{H_2}$N), 1.15–0.6m 5H,CO—![cyclopropyl]). | — | — |

TABLE 5-continued

| Ex. No. | R | Compound 11 NMR:δ$^{CDCl_3}$ | Compound 12 n | mp (°C.) |
|---|---|---|---|---|
| 14 | (phenyl, H) | 3.57s(2H, PhCH$_2$N). | 1 | 114 ~ 115(dec.) |
| 15 | —CH$_2$Cl | 4.08t(2H,J = 6Hz,OCH$_2$—), 4.07s(2H, COCH$_2$—), 3.62s(2H, (ring)NCH$_2$—). | — | — |
| 16 | —CH=CH$_2$ | 3.50s(2H,NCH$_2$), 5.42 ~ 6.15m(CH=CH$_2$). | 1 | 77 ~ 79(dec.) |
| 17 | —CH=CHPh | 3.62s(2H,NCH$_2$), 6.42d(1H,J = 6Hz, CH). | 1 | 117 ~ 120(dec.) |
| 18 | —N(CH$_3$)$_2$ | 4.05t(2H,J = 6Hz,OCH$_2$), 3.58s(2H, (ring)NCH$_2$—),2.10s(6H,CH$_3$). | — | — |
| 19 | —N(C$_2$H$_5$)$_2$ | 3.55s(2H,PhCH$_2$), 1.10d(6H,J = 7Hz, NCH$_2$CH$_3$). | — | — |
| 20 | —Ph | 3.57s(2H,NCH$_2$) | 1 | 140 ~ 142(dec.) |
| 21 | —CH$_2$Ph | 3.95t(2H,J = 6Hz,OCH$_2$), 3.58(4H, (ring)NCH$_2$—, COCH$_2$). | 1 | 142 ~ 144(dec.) |
| 22 | —CHOPh / CH$_3$ | 3.55s(2H,PhCH$_2$N), 1.53d(3H, J = 7Hz,—CH(CH$_3$)OPh). | 1 | 141 ~ 142.5(dec.) |
| 23 | CH$_3$O-phenyl | 3.85s(3H,OCH$_3$), 3.60s(2H,NCH$_2$). | 1 | 122 ~ 124(dec.) |
| 24 | phenyl-OCH$_3$ | 3.83s(3H,OCH$_3$), 3.60s(2H,NCH$_2$). | 1 | 138 ~ 141(dec.) |
| 25 | phenyl-OC$_2$H$_5$ | 3.55s(2H,PhCH$_2$N), 1.32t(3H, J = 7Hz,OCH$_2$CH$_3$). | — | — |
| 26 | Cl-phenyl | 4.08t(2H,J = 6Hz,OCH$_2$), 3.57s(2H, NCH$_2$). | 1 | 158 ~ 160(dec.) |
| 27 | phenyl-Cl | 4.18t(2H,6Hz,OCH$_2$),3.70s(2H, NCH$_2$). | 1 | 165 ~ 167(dec.) |
| 28 | phenyl-COOCH$_3$ | 3.93s(3H,COOCH$_3$), 3.58s(2H, PhCH$_2$N). | 1 | 168 ~ 169 |
| 29 | CH$_3$O, CH$_3$, NO$_2$-phenyl | 4.10t(2H,J = 6Hz,OCH$_2$), 3.92s(3H, OCH$_3$),3.58s(2H, (ring)NCH$_2$), 2.67 (3H,CH$_3$). | 1 | 154 ~ 156(dec.) |
| 30 | CH$_3$O, OCH$_3$, NO$_2$-phenyl | 4.12t(2H,J = 6Hz,OCH$_2$),3.97s(3H, OCH$_3$) | 1 | 120 ~ 123(dec.) |
| 31 | PhCO-phenyl | 4.03t(2H,J = 6Hz,OCH$_2$), 3.43s(2H, (ring)NCH$_2$). | 1 | 143 ~ 146(dec.) |
| 32 | pyridyl (N) | 4.23t(2H,J = 6Hz,OCH$_2$), 3.60s(2H, NCH$_2$) | 2½ | 129 ~ 131(dec.) |
| 33 | pyridyl (N) | — | 2½ | 153 ~ 155(dec.) |
| 34 | thienyl (S) | 4.13t(2H,J = 6Hz,OCH$_2$), 3.63s(2H, NCH$_2$). | 1 | 147 ~ 149(dec.) |
| 35 | isoxazolyl-Ph | 8.2 ~ 7.8m(Ph), 3.57s(2H,PhCH$_2$N). | 1 | 190 ~ 192(dec.) |

TABLE 5-continued

| Ex. No. | Compound 11 R | NMR: $\delta^{CDCl_3}$ | Compound 12 n | mp (°C.) |
|---|---|---|---|---|
| 36 | ![naphthyl] | 8.2 ~ 7.1m(![naphthyl]), 3.53s(2H,PhCH$_2$N). | 1 | 149 ~ 151(dec.) |
| 37 | ![methylnaphthyl] | 8.1 ~ 7.2m(7H, —![naphthyl]—), 3.50s(2H, PhCH$_2$N) (d$_6$-DMSO). | 1 | 170 ~ 171(dec.) |

EXAMPLE 38

Preparation of 3-(2-salicylamidoethyl)thiomethyl-1-dimethylaminomethylbenzene

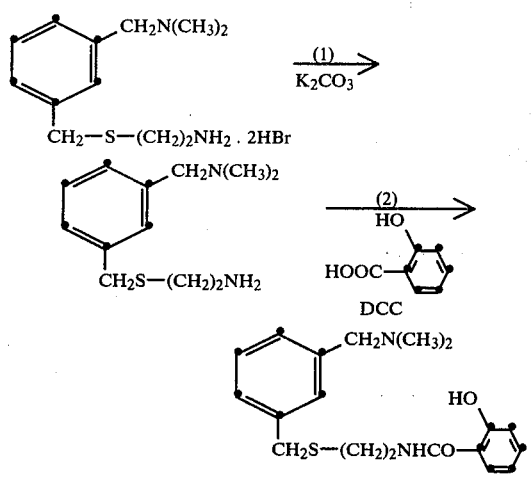

(1) Compound 4 (1 g; 2.63 mmoles) is treated with aqueous potassium carbonate and the solvent is evaporated under reduced pressure. The residue is extracted with ethanol and the extract is concentrated under reduced pressure to give Compound 13.

(2) To a solution of Compound 13 in methylene chloride (10 ml) are added salicyclic acid (0.363 g; 2.63 mmoles) and DCC (0.543 g; 2.63 mmoles) at room temperature, and the mixture is stirred for 4 hours. The resulting crystals are filtered off and the filtrate is washed with aqueous sodium hydrogencarbonate, dried, and concentrated under reduced pressure. The oily residue is purified by chromatography on a column of silica gel with methanol to give Compound 14 as an oily product (0.49 g).

Yield 54%

NMR: $\delta^{CDCl_3}$ 2.23S(6H, CH$_3$x2), 3.37s(2H, NCH$_2$), 3.72s(2H, SCH$_2$)

IR: $\nu^{film}$ 3300, 1680, 1635 cm$^{-1}$.

The above oily product 14 is treated with oxalic acid-/ethanol and recrystallized from ethanol-ethyl acetate to give the monooxalate.

Oxalate of Compound 14
mp. 72° ~ 74° C. (dec.)

Elemental Analysis (for C$_{19}$H$_{24}$N$_2$O$_2$S.(COOH)$_2$): Calcd (%): C, 58.05; H, 6.03; N, 6.45; S, 7.38. Found (%): C, 58.07; H, 6.02; N, 6.51; S, 7.10.

EXAMPLE 39

The following compound is prepared from Compound 13 and benzoylformic acid in the same manner as in Example 39.

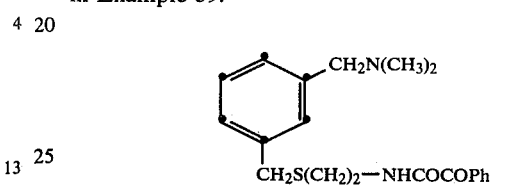

NMR: $\delta^{CDCl_3}$ 3.78(2H, PhCH$_2$S—), 3.42(2H, PhCH$_2$N—), 2.23(6H, CH$_3$).

Oxalate
mp. 98° ~ 100° C. (dec.)

Elemental Analysis (for C$_{20}$H$_{24}$N$_2$SO$_2$.(COOH)$_2$): Calcd (%): C, 59.18; H, 5.87; N, 6.27; S, 7.18. Found (%): C, 58.65; H, 6.00; N, 6.31; S, 7.30.

EXAMPLE 40

Preparation of 3-[3-(2-methylthio-2-phenylacetamido)propoxy]-1-(1-pyrrolidinylmethyl)benzene

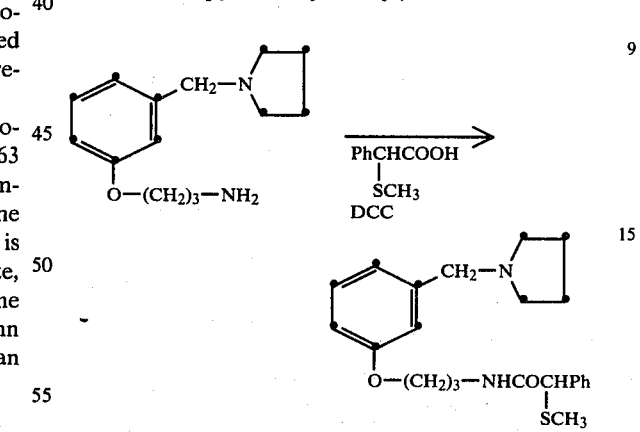

To a solution of Compound 9 (0.628 g; 2.7 mmoles) and DCC (1.42 g; 9 mmoles) in dry methylene chloride (6 ml) is added 2-methylthio-2-phenylacetic acid (0.929 g; 5 mmoles) little by little, and the mixture is stirred at room temperature for 16 hours. The resulting precipitate is filtered off and the filtrate is concentrated under reduced pressure. The residue is dissolved in ethyl acetate, and if required, the further precipitate is filtered off. The filtrate is concentrated under reduced pressure to give an oily crude product, which is chromatographed (silica gel 40 g/methanol) to give Compound 15 (0.870 g).

Yield 81.5%

NMR: $\delta^{CDCl_3}$ 3.60S(2H, PhC$\underline{H}_2$—N), 2.07s(3H, SC$\underline{H}_3$).

IR: $\nu^{film}$ 3300, 1640, 1520 cm$^{-1}$.

Monooxalate (recrystallized from ethanol-ether) mp. 98°~100° C. (dec.)

Elemental Analysis (for $C_{23}H_{30}O_2N_2S.(COOH)_2$): Calcd (%): C, 61.45; H, 6.60; N, 5.73. Found (%): C, 61.51; H, 6.65; N, 5.68.

EXAMPLES 41 TO 68

The following compounds in Table 6 are prepared from Compound 9, the carboxylic acid and DCC in the same manner as in Example 40.

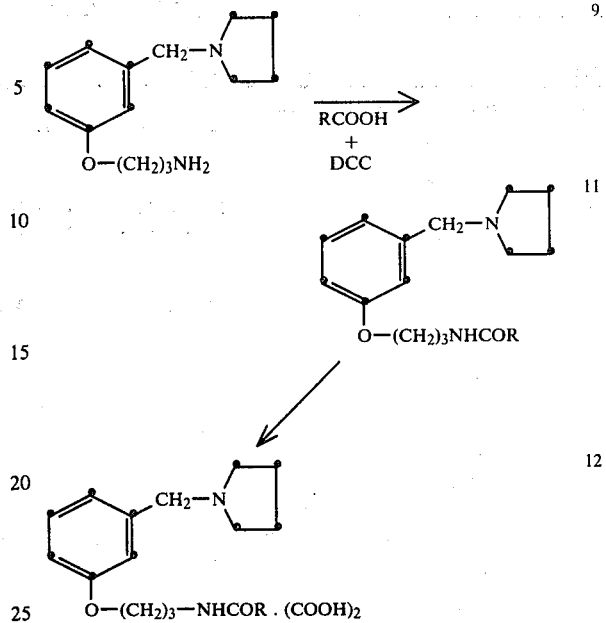

TABLE 6

| Ex. No. | R | Solvent | Compound 11 NMR:$\delta^{CDCl_3}$ | Compound 12 n | mp (°C.) |
|---|---|---|---|---|---|
| 41 | —H | CH$_2$Cl$_2$ | 8.15s(1H,CHO), 3.62s(2H,N—CH$_2$). | 1 | 106 ~ 108 |
| 42 | —(CH$_2$)$_2$CH=CH$_2$ | " | 6.10 ~ 5.57m(1H,CH), 4.90 ~ 5.23m (1H,CH), 3.60s(2H,NCH$_2$), 2.30 m(4H,CH$_2$CH$_2$). | 1 | 94 ~ 96 |
| 43 | —CH=C(CH$_3$)$_2$ | " | 3.60s(2H,NCH$_2$), 2.17s, 1.85s (6H,CH$_3$ × 2). | 1 | 128 ~ 130 |
| 44 | —⌬—OH | " | 3.92t(2H, J = 6Hz,OCH$_2$), 3.73s (2H,CH$_2$) | 1 | 128 ~ 130 |
| 45 | —⌬—F | THF | 4.03t(2H, J = 6Hz,PhOCH$_2$), 3.53s (2H,PhCH$_2$N). | — | — |
| 46 | —⌬—NO$_2$ | DMF | 8.27, 7.93d(2H, each, J = 9Hz, CO—⌬—NO$_2$), 3.57s(2H,PhCH$_2$N) | 1 | 108 ~ 110(dec.) |
| 47 | NH$_2$ (ortho) | THF | IR(film) 3320,1660-1580, 1530 cm$^{-1}$. | 1½ | 159 ~ 160(dec.) |
| 48 | —⌬—NH$_2$ | DMF | mp. 116 ~ 118° C. | — | — |
| 49 | —⌬—N(CH$_3$)$_2$ | CH$_2$Cl$_2$ | 3.57s(2H,PhCH$_2$N), 2.97s(6H, (CH$_3$)$_2$N) | 1 | 180 ~ 181(dec.) |
| 50 | —⌬—NHCOCH$_3$ | CH$_2$Cl$_2$ -DMSO (1:1) | 3.58s(2H,PhCH$_2$N), 2.15s(3H, NHCOCH$_3$). | 1 | 181 ~ 182(dec.) |
| 51 | —⌬—SO$_2$NH$_2$ | DMF | 8.00b(4H,PhH), 4.13t(2H, J = 6Hz,PhOCH$_2$), 3.63s(2H, PhCH$_2$N). | 1 | 200 ~ 201(dec.) |
| 52 | COOCH$_3$ ⌬ | " | 3.92s(3H,COOCH$_3$), 3.58s(2H, PhCH$_2$N) | 1 | 120 ~ 122 |
| 53 | —⌬—CN | CH$_2$CN -DMF (3:1) | 7.98b(4H, CO—⌬—CN), 3.47s(2H,PhCH$_2$N) (d$_6$-DMSO). | 1 | 150 ~ 152(dec.) |

TABLE 6-continued

| Ex. No. | R | Solvent | Compound 11 NMR:$\delta^{CDCl_3}$ | Compound 12 n | mp (°C.) |
|---|---|---|---|---|---|
| 54 | 2,3-(CH$_3$O)$_2$-phenyl (CH$_3$O, OCH$_3$) | CH$_2$Cl$_2$ | 3.95s(3H,OCH$_3$), 3.90s(3H, OCH$_3$), 3.60s(2H,NCH$_2$). | 1 | 125 ~ 126(dec.) |
| 55 | 2,4-(CH$_3$O)$_2$-phenyl | " | 7.88b(1H,NH), 3.87s(3H,OCH$_3$), 3.83s(3H,OCH$_3$), 3.58s(2H, NCH$_2$). | 1 | 114 ~ 117 |
| 56 | 2,5-(OCH$_3$)$_2$-phenyl | " | 3.92s(6H,OCH$_3$ × 2), 3.60s(2H, NCH$_2$). | 1 | 128 ~ 129(dec.) |
| 57 | 2,3,4-(OCH$_3$)$_3$-phenyl | " | 3.87s(9H,OCH$_3$ × 3), 3.58s(2H, NCH$_2$). | 1 | 77 ~ 78 |
| 58 | 2-NO$_2$-phenyl | CH$_3$CN | 3.98s(3H,COOCH$_3$), 3.57s(2H, PhCH$_2$N). | 1 | 164 ~ 165(dec.) |
| 59 | —CH$_2$-C$_6$H$_4$-OH | CHCl$_3$ | mp. 143 ~ 145° C. | — | — |
| 60 | pyridyl | CH$_2$Cl$_2$ | 4.03t(2H,J = 6Hz,OCH$_2$), 3.60s (2H,NCH$_2$). | 1½ | 138 ~ 140(dec.) |
| 61* | pyrrolidinyl (H, N) | " | 4.05t(2H, J = 6Hz,OCH$_2$), 3.60s (2H,NCH$_2$), 2.63-1.73m(6H, N ). | 2 | 170 ~ 172 |
| 62 | pyrrolidinon-yl | " | — | 1½ | 122 ~ 125 |
| 63 | —CH$_2$-oxadiazolyl-Ph | " | 3.92(2H,NHCOCH$_2$), 3.53(2H, PhCH$_2$N) | 1 | 155 ~ 156(dec.) |
| 64 | thiophen-ketone | " | 7.23d, 7.12d(1H, each J = 11 Hz, S=O). | 1 | 133 134(dec.) |
| 65 | —CH$_2$—N(tetrazolyl) | THF-CH$_3$CN (1:1) | 9.17s(1H,N=CH—N), 3.60s (2H,PhCH$_2$N). | 1 | 161 ~ 162 |
| 66 | phenyl-tetrazolyl | DMF | 9.12s(1H,NCH—N), 3.55s (2H,PhCH$_2$N). | 1 | 157 ~ 158(dec.) |
| 67 | phenyl-tetrazolyl-NH | " | IR(film) 1640, 1550 cm$^{-1}$. | 1 | 130 ~ 135 |
| 68 | oxazinyl-COCH$_3$ | CH$_2$Cl$_2$ | 3.57s(2H,PhCH$_2$N), 2.17s(3H, NCOCH$_3$). | 1 | 157 ~ 159(dec.) |

*This product is obtained by reacting the amine (9) with N-carbobenzoxypyrrolidine-2-carboxylic acid over DCC and treating the N-protected intermediate with 30% HBr-acetic acid at room temperature for 2 hours.

EXAMPLE 69

Preparation of 3-(3-nipecotamidopropoxy)-1-(1-pyrrolidinylmethyl)benzene

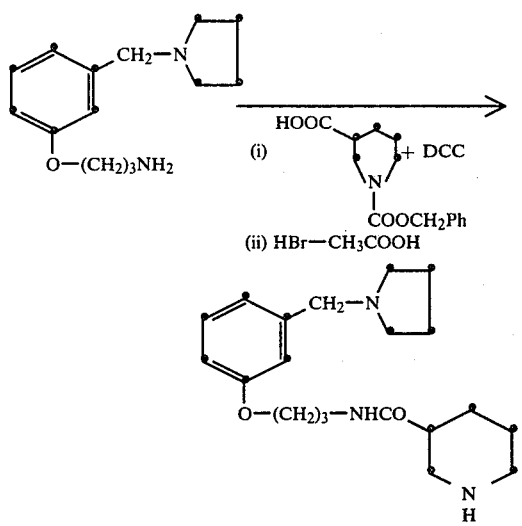

To a solution of Compound 9 (0.978 g) and N-carbobenzoxynipecotic acid (1.052 g) in chloroform (20 ml) is added DCC (0.9 g), and the mixture is stirred at room temperature for 2 days. The reaction mixture is washed with water, dried, and evaporated. The residue is chromatographed on a column of silica gel and eluted with methanol. The resulting oily product (0.4 g) is mixed with 30% hydrobromic acid-acetic acid (1.5 ml), and the mixture is stirred at room temperature for 1 hour and mixed with ether. The resulting viscous product is separated and neutralized with aqueous sodium hydrogencarbonate and the solvent is evaporated. The residue is extracted with chloroform and the extract is concentrated to give Compound 15.

Compound 15 is treated with oxalic acid and recrystallized from ethanol to give dioxalate of Compound 15. mp. 118°~120° C. (dec.)

Elemental Analysis (for $C_{20}H_{31}N_3O_2 \cdot 2(COOH)_2$): Calcd (%): C, 53.03; H, 6.86; N, 7.73. Found (%): C, 53.18; H, 6.68; N, 7.71.

EXAMPLE 70

Preparation of 3-(2-acetamidoethyl)thiomethyl-1-dimethylaminomethylbenzene

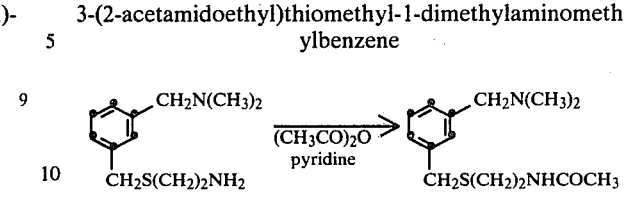

To a solution of Compound 13 (0.5 g) in dry pyridine (2 ml) is added acetic anhydride (2 ml), and the mixture is stirred for 3 hours. The reaction mixture is pured into icy water, neutralized with 5% sodium hydrogencarbonate, and extracted with ethyl acetate. The extract is washed with water, dried over anhydrous sodium sulfate, and concentrated to give crude Compound 16 (0.229 g), which is chromatographed on silica gel (20 g) and eluted with methanol to give Compound 16 (0.168 g) as a pure product.

Yield 28%

NMR: $\delta^{CDCl_3}$ 2.15s(3H, NHCOC$\underline{H}_3$), 2.45s(6H, N(C$\underline{H}_3$)$_2$), 3.92s(2H, PhC$\underline{H}_2$S), 3.62s(2H, PhC$\underline{H}_2$N—)

IR: $\nu^{film}$ 3300, 1650, 1550 cm$^{-1}$.

Compound 16 is treated with oxalic acid and recrystallized from ethanol to give monooxalate of Compound 16.

mp. 135°~136° C.

EXAMPLES 71 TO 74

Compounds shown in Table 7 are prepared from Compound 13 and carboxylic anhydride in the same manner as in Example 70.

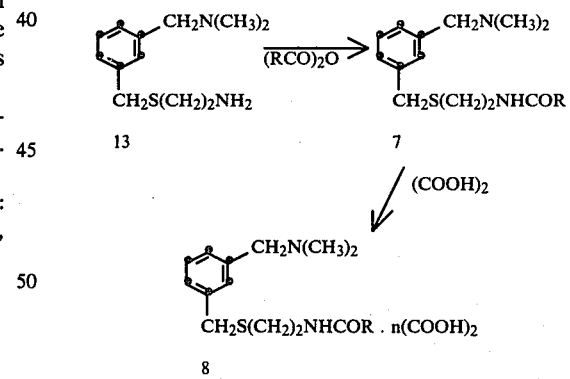

TABLE 7

| Ex. No. | R | Compound 7 NMR: $\delta^{CDCl_3}$ | Compound 8 n | mp (°C.) |
|---|---|---|---|---|
| 71 | —CF$_3$ | 3.72s(2H,PhCH$_2$N), 3.42s(2H, PhCH$_2$N), 2.22s(6H,CH$_3$ × 2). | 1 | 133~134 |
| 72 | —(CH$_2$)$_2$CH$_3$ | 5.87b(1H,NH), 3.72s(2H,NCH$_2$), 3.43s(2H,NCH$_2$), 2.25s(6H,CH$_3$ × 2), 0.95t(3H,J = 7Hz). | 1 | 119~121 |
| 73 | —CH(CH$_3$)$_2$ | 5.87b(1H,NH), 3.73s(2H,SCH$_2$), 3.43s(2H,NCH$_2$), 2.25s(6H,CH$_3$ × 2), 1.15d(6H,J = 7Hz,CH$_3$ × 2). | 1 | 140~142(dec.) |
| 74 | —Ph | 7.00b(1H,NH), 4.02s(2H,SCH$_2$), 3.53s(2H,NCH$_2$), 2.78s(6H,CH$_3$ × 2). | 1 | 149~151 |

EXAMPLE 75

Preparation of
3-(2-phthalamidoethyl)thiomethyl-1-dimethylaminomethylbenzene

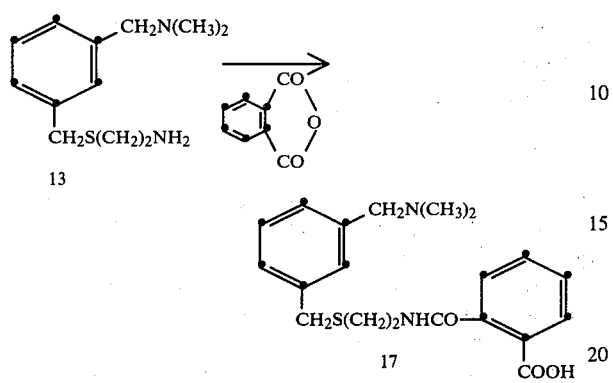

A suspension of Compound 13 (1.12 g), phthalic anhydride (0.74 g) in water (20 ml) is stirred for 2 hours, allowed to stand overnight, and concentrated under reduced pressure. The resulting residue is chromatographed on a column of silica gel eluting with methanol to give Compound 17 (1.6 g) as an oily product.

NMR: $\delta^{CDCl_3}$ 3.93(2H, PhC$\underline{H_2}$S), 3.73(2H, PhC$\underline{H_2}$N), 2.60(6H, CH$_3$), 9.87b(1H, —OH).

The oily product is treated with oxalic acid and recrystallized from ethanol to give monooxalate of Compound 17 (2 g).

m.p. ca 80° C.

Elemental Analysis (for C$_{20}$H$_{24}$N$_2$SO$_3$·(COOH)$_2$·H$_2$O): Calcd (%): C, 54.99; H, 5.87; N, 5.83; S, 6.67. Found (%): C, 55.41; H, 6.18; N, 5.81; S, 7.01.

EXAMPLE 76

Preparation of
3-[2-(phenylthiocarbonylamino)ethylthiomethyl]-1-dimethylaminomethylbenzene

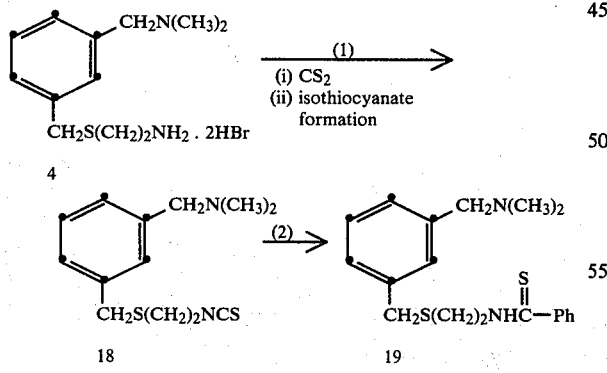

(1) To a suspension of sodium hydride (65% oil dispersion; 0.122 g; 3.3 mmoles) in tetrahydrofuran (3.3 ml) are added Compound 4 (0.419 g; 1.1 mmoles), carbon disulfide (0.4 ml) and dimethylformamide (0.3 ml), and the mixture is stirred at −5° to 0° C. for 50 minutes. 2-Bromo-3-ethyl-4-phenylthiazolium fluoroborate (0.394 g; 1.1 mmoles) and triethylamine (0.16 ml) are added thereto. The reaction mixture is stirred at 0° to 10° C. for 2 hours, mixed with water and extracted with ethyl acetate. The organic layer is washed with water, dried, and evaporated under reduced pressure. The residue is purified by chromatography (silica gel/acetone) to give Compound 18 (0.230 g).

Yield 80.4%

(2) To a solution of Compound 18 (0.100 g; 0.375 mmoles) in dry tetrahydrofuran (1 ml) is added phenyl magnesium bromide (0.56 mg) at −10° C., and the mixture is stirred at 5° to 8° C. for 6 hours. The reaction mixture is mixed with ethyl acetate and 15% aqueous ammonium chloride. The ethyl acetate layer is washed with water, dried, and concentrated under reduced pressure. The residue is purified by columnar chromatography (silica gel/methanol) to give Compound 19 as an oily product.

Yield 93%

NMR: $\delta$CDCl$_3$ 2.18s(6H, CH$_3$×2), 2.83t(J=7 Hz, —S—CH$_2$), 3.38s(2H, NCH$_2$), 3.77s(2H, SCH$_2$), 8.17b (1H, NH).

IR: $\nu^{film}$ 3220, 1250 cm$^{-1}$.

Compound 19 is treated with oxalic acid/ethanol and recrystallized from ethanol to give monooxalate. m.p. 137°~139° C. (dec.)

Elemental Analysis (for C$_{19}$H$_{24}$N$_2$S$_2$·(COOH)$_2$): Calcd (%): C, 58.04; H, 6.03; N, 6.45. Found (%): C, 58.21; H, 6.04; N, 6.36.

EXAMPLE 77

Preparation of
3-[(D-phenylglycinamidoethyl)thiomethyl]-1-dimethylaminomethylbenzene

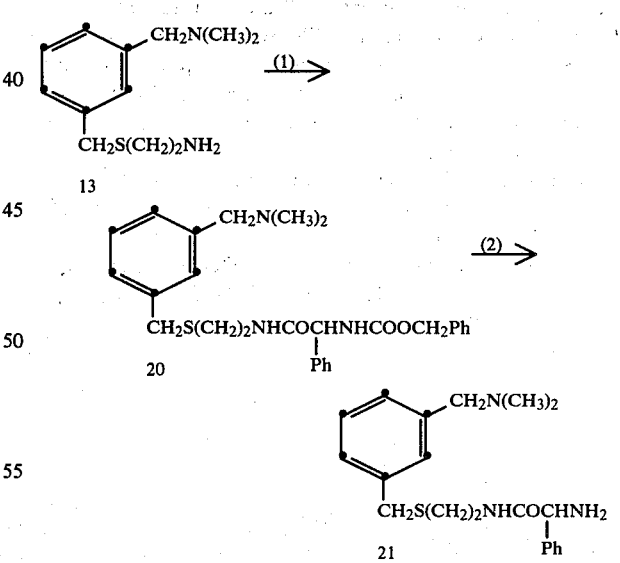

(1) To a solution of N-(carbobenzoxy-D-phenylglycyl)succinimide. (1.53 g) in dimethylformamide (10 ml) are added Compound 13 (0.9 g) and N-ethylmorpholine (0.46 g) at −20° C., and the mixture is stirred at −20° C. for 1 hour and at room temperature for 7 hours, then allowed to stand overnight. The reaction mixture is evaporated under reduced pressure. The residue is extracted with chloroform and the extract is washed with water, dried, and concentrated. The resulting residue is purified by chromatography (silica gel/methanol) to give Compound 20 as an oily product.

NMR: $\delta^{CDCl_3}$ 6.33b(1H, —NH—), 5.08 (2H, C$\underline{H_2}$), 3.62(2H, PhC$\underline{H_2}$S), 3.42(2H, PhC$\underline{H_2}$N), 2.20(6H, C$\underline{H_3}$)

Compound 20 is mixed with 30% hydrogen bromideacetic acid. After stirring for 4 hours, to the mixture is added ether. The resulting hygroscopic crystals are filtered off. The filtrate is neutralized with aqueous sodium hydrogencarbonate and extracted with chloroform. The extract is dried and concentrated to give Compound 21 as an oily product.

NMR: $\delta^{CDCl_3}$ 4.48(1H, —CH—), 3.70(2H, PhC$\underline{H_2}$S—), 3.40(2H, PhC$\underline{H_2}$N), 2.22(6H, CH$_3$), 1.83b(2H, NH$_2$)

Compound 21 is treated with oxalic acid and recrystallized from ethanol to give the dioxalate of Compound 21.

mp. 136°~138° C. (dec.)

Elemental Analysis (for C$_{20}$H$_{27}$N$_3$SO.2(COOH)$_2$): Calcd (%): C, 53.62; H, 5.81; N, 7.82; S, 5.96. Found (%): C, 53.35; H, 6.00; N, 7.56; S, 6.20.

EXAMPLE 78

Preparation of 3-[3-(2-furylcarbonamido)propoxy]-1-(1-pyrrolidinylmethyl)benzene

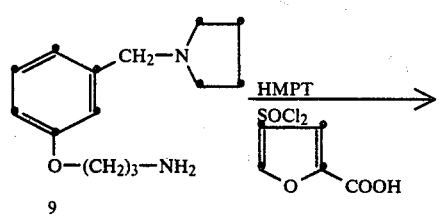

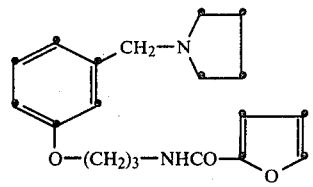

To a solution of 2-furancarboxylic acid (0.337 g) in HMPT (4 ml) and acetonitrile (0.5 ml) is added thionyl chloride (0.187 ml) at −9° to −5° C., and the mixture is stirred at −5° C. for 20 minutes. Compound 9 (0.469 g) is added thereto, and the resultant mixture is warmed to room temperature, stirred for 3 hours, then allowed to stand overnight. The reaction mixture is neutralized with aqueous sodium hydrogencarbonate and extracted with ether. The extract is washed with water, dried, and concentrated to give Compound 22 as an oily product.

NMR: $\delta^{CDCl_3}$ 4.16t(2H, J=6 Hz, O—C$\underline{H_2}$—), 3.57s (2H, 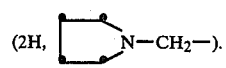 N—CH$_2$—).

Compound 22 is treated with oxalic acid and recrystallized from ethanol to give oxalate (0.7 g).

mp. 90°~92° C. (dec.)

Elemental Analysis (for C$_{19}$H$_{24}$N$_2$O$_3$.(COOH)$_2$): Calcd (%): C, 60.28; H, 6.27; N, 6.69. Found (%): C, 59.66; H, 6.08; N, 6.65.

EXAMPLES 79 TO 80

Compounds shown in Table 8 are prepared in the same manner as in Example 78.

TABLE 8

| Ex. No. | R | Compound 11 NMR : $\delta^{CDCl_3}$ | Compound 12 n | mp (°C.) |
|---|---|---|---|---|
| 79 | (thiophene-Br) | mp. 126~128° C. | — | — |
| 80 | (phenyl-N(CH$_3$)$_2$) | 4.13t(2H,J = 6Hz,OCH$_2$), 3.60s(2H, NCH$_2$),2.97s(6H,CH$_3$ × 2). | 2 (H$_2$O) | 115~117(dec.) |

EXAMPLE 81

Preparation of 3-[2-(2-piperidinoacetamido)propoxy]-1-(1-pyrrolidinylmethyl)benzene

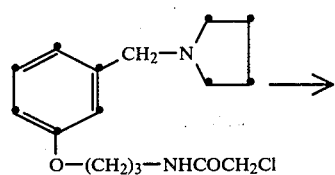

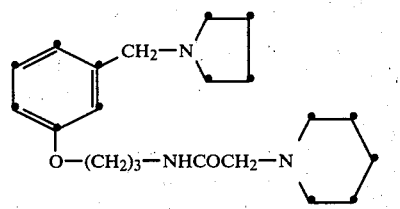

To a solution of Compound 23 (0.5 g) prepared in Example 15 in chloroform (10 ml) is added piperidine (0.3 ml), and the mixture is stirred for 1 hour, then allowed to stand overnight. The reaction mixture is washed with water, dried, and evaporated to give Compound 24 as an oily product.

NMR: $\delta^{CDCl_3}$ 4.03t(2H, J=6 Hz, O—C$\underline{H}_2$—), 3.58s

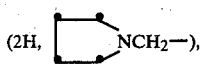

2.95s(2H, COC$\underline{H}_2$)

Compound 24 is treated with oxalic acid and recrystallized from ethanol to give oxalate (0.7 g).

mp. 129°~131° C. (dec.)

Elemental Analysis (for $C_{21}H_{31}N_3O_2 \cdot 2(COOH)_2 \cdot \frac{1}{2}H_2O$): Calcd (%): C, 54.94; H, 6.64; N, 7.69. Found (%): C, 55.27; H, 6.99; N, 7.46.

EXAMPLE 82

The following compound is prepared from Compound 23 and morpholine in the same manner as in Example 81.

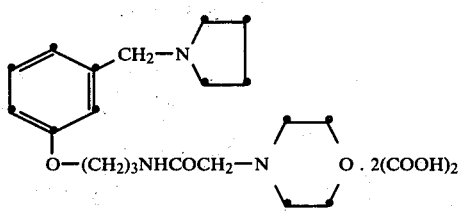

mp. 112°~114° C.

Elemental Analysis (for $C_{20}H_{31}N_3O_3 \cdot 2(COOH)_2$): Calcd (%): C, 53.23; H, 6.51; N, 7.76. Found (%): C, 53.82; H, 6.68; N, 7.61.

EXAMPLE 83

The following compound is prepared from Compound 23, diethylamine, methanol, and potassium iodide in the same manner as in Example 81.

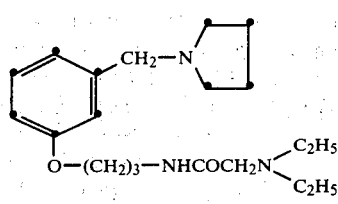

NMR: $\delta^{CDCl_3}$ 4.08t(2H, J=6 Hz, O—C$\underline{H}_2$—), 3.90s

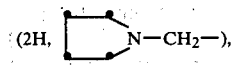

3.03s(2H, COC$\underline{H}_2$—), 2.58q(4H, J=7 Hz, N—C$\underline{H}_2$CH$_3$), 1.00t(6H, J=7 Hz, NCH$_2$C$\underline{H}_3$)

EXAMPLE 84

Preparation of 3-(3-acetamidopropoxy)-1-(1-pyrrolidinylmethyl)benzene

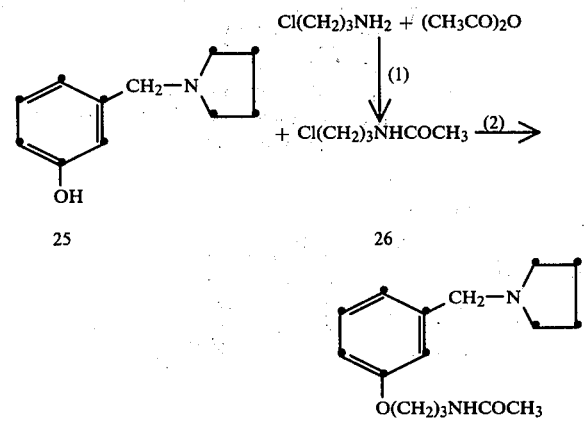

(1) To a solution of 3-chloropropylamine (12 g; 92 mmoles) in dry pyridine (20 ml) is added acetic anhydride (18.5 g; 185 mmoles) under ice-cooling with stirring, and the mixture is stirred at room temperature for 20 hours. The reaction mixture is concentrated under reduced pressure. The residue is dissolved in chloroform, and the solution is washed with 10% acetic acid, aqueous sodium hydrogencarbonate and then water, dried over anhydrous sodium sulfate and concentrated to give Compound 26 (4.95 g).

Yield 39.5%

(2) To a solution of sodium hydride (50% mineral oil suspension; 0.149 g; 3.1 mmoles) in dry dimethylformamide (2 ml) is added a solution of Compound 25 (0.585 g; 3.3 mmoles) in dry dimethylformamide (4 ml). During the course of the reaction, the violent evolution of hydrogen gas is noted. The reaction mixture is stirred at room temperature for 30 minutes. To the resulting clear solution is added dropwise a solution of N-acetyl-γ-chloropropylamine (0.5 g; 3.7 mmoles) in dry dimethylformamide (3 ml) at 0° to 5° C. over a period of 20 minutes. The reaction mixture is stirred at room temperature for 20 hours, poured into water (100 ml), and extracted with ethyl acetate. The organic layer is washed with brine, dried over anhydrous sodium sulfate, and concentrated to give an oily product (2.064 g), which is purified by chromatography (silica gel (50 g)/ethanol) to give Compound 27 (0.9 g).

Yield 98.6%

NMR: $\delta^{CDCl_3}$ 3.57s(2H, N—CH$_2$), 1.95s(3H, COCH$_3$), 5.90bs (1H, NH).

IR: $\nu^{film}$ 1640 cm$^{-1}$.

Compound 27 is treated with oxalic acid and recrystallized from ethanol—ether to give monoooxalate.

mp. 104°~108° C. (dec.)

Elemental Analysis (for C$_{16}$H$_{24}$O$_2$N$_2$.(COOH)$_2$): Calcd (%): C, 59.00; H, 7.15; N, 7.65. Found (%): C, 58.80; H, 7.00; N, 7.57.

EXAMPLE 85

Preparation of 3-(3-acetamidopropoxy)-1-(1-pyrrolidinylmethyl)benzene

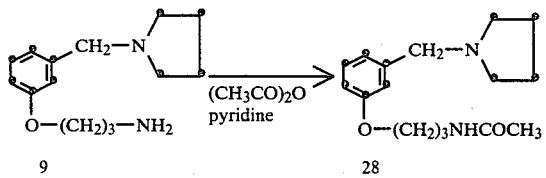

To a solution of Compound 9 (0.189 g; 0.807 mmole) in dry pyridine (5 ml) is added acetic anhydride (0.100 g; 0.964 mmole), and the mixture is stirred at room temperature overnight and concentrated under reduced pressure. The residue is mixed with sodium hydrogencarbonate-saturated brine and extracted with chloroform. The extract is dried and concentrated. The residue is purified by columnar chromatography (silica gel/methanol) to give Compound 28 (0.13 g) as an oily product.

Yield 58.3%

NMR: $\delta^{CDCl_3}$ 3.57s(2H, N—CH$_2$), 1.95s(3H, COCH$_3$), 5.90bs (1H, NH).

IR: $\nu^{film}$ 1640 cm$^{-1}$.

Compound 28 is treated with oxalic acid/ethanol and recrystallized from ethanol—ether to give oxalate.

mp. 104°~108° C. (dec.)

Elemental Analysis (for C$_{16}$H$_{24}$N$_2$O$_2$.(COOH)$_2$): Calcd (%): C, 59.00; H, 7.15; N, 7.65. Found (%): C, 58.80; H, 7.00; N, 7.57.

EXAMPLE 86

The following compound is prepared from Compound 9 and trifluoroacetic anhydride in the same manner as in Example 85.

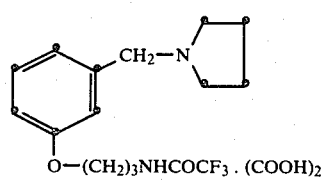

mp. 141°~142° C.

Elemental Analysis (for C$_{16}$H$_{21}$N$_2$F$_3$O$_2$.(COOH)$_2$): Calcd (%): C, 51.43; H, 5.51; N, 6.66; F, 13.56. Found (%): C, 51.61; H, 5.45; N, 6.52; F, 13.49.

EXAMPLE 87

Preparation of 3-(3-acetamidopropoxy)-1-dimethylaminomethylbenzene

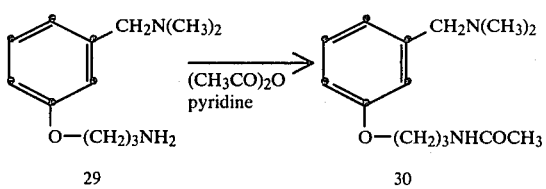

A solution of Compound 29 (0.4 g) and acetic anhydride (0.4 g) in pyridine (1 ml) is stirred overnight and concentrated under reduced pressure. The residue is mixed with ethyl acetate and aqueous sodium hydrogen-carbonate. The organic layer is separated, washed with saturated brine, dried over anhydrous sodium sulfate, and concentrated under reduced pressure. The residue is chromatographed (silica gel/methanol) to give Compound 30 as a colorless oily product (0.25 g). This is treated with oxalic acid-ethanol and recrystallized from ethanolether to give oxalate (0.2 g).

mp. 111°~114° C.

Elemental Analysis (for C$_{14}$H$_{22}$N$_2$O$_2$.(COOH)$_2$): Calcd (%): C, 56.46; H, 7.11; N, 8.23. Found (%): C, 56.31; H, 7.06; N, 8.14.

EXAMPLE 88

Preparation of 3-(3-benzoylamidopropoxy)-1-dimethylaminomethylbenzene

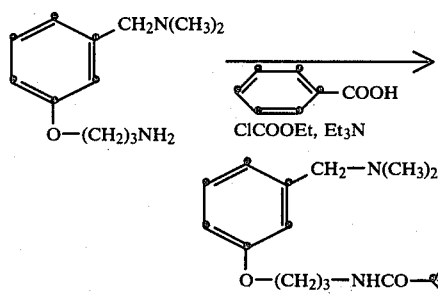

To a solution of benzoic acid (0.5 g) and triethylamine (0.45 g) in tetrahydrofuran (10 ml) is added dropwise a solution of ethyl chloroformate (0.4 g) in tetrahydrofuran (2 ml) at 0° C., and the mixture is stirred for 15 minutes. A solution of Compound 29 (0.4 g) in tetrahydrofuran (2 ml) is added thereto. The resulting mixture is gradually warmed to room temperature and stirred overnight. Most of tetrahydrofuran is evaporated under reduced pressure. The residue is distributed to dichloromethane and water. The organic layer is separated, dried over anhydrous sodium sulfate, and concentrated under reduced pressure. The residue is purified by columnar chromatography (silica gel/methanol) to give Compound 31 as a colorless oily product (0.45 g)..

A solution of Compound 31 (0.35 g) in ethanol (1 ml) is treated with oxalic acid (0.2 g) and recrystallized from ethanol to give oxalate (0.15 g).

mp. 157°~159° C.

Elemental Analysis (for $C_{19}H_{24}N_2O_2\cdot(COOH)_2$): Calcd (%): C, 62.67; H, 6.51; N, 6.96. Found (%): C, 62.34; H, 6.53; N, 6.96.

EXAMPLE 89

Preparation of 3-[3-(4-methyl-5-imidazolylcarbonamido)propoxy]-1-dimethylaminomethylbenzene

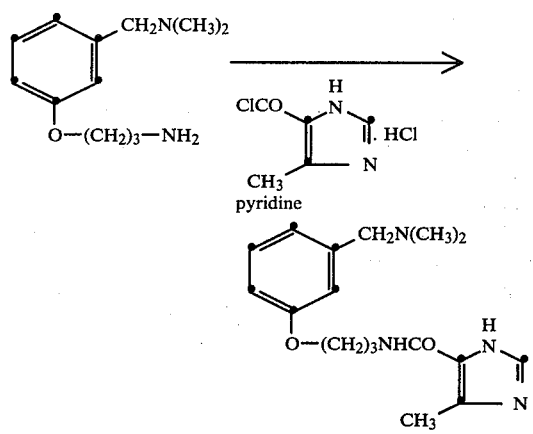

A solution of Compound 29 (0.42 g) and 4-methyl-5-imidazolylcarbonyl chloride hydrochloride (1.05 g) in pyridine (10 ml) is stirred at room temperature overnight and pyridine is evaporated under reduced pressure. The residue is distributed to aqueous sodium hydrogencarbonate and chloroform. The organic layer is separated, washed with saturated brine, dried over anhydrous sodium sulfate, and concentrated. The oily residue is chromatographed (silica gel/methanol) to give Compound 32 (0.35 g) as a viscous oily product.

A solution of Compound 32 (0.35 g) in ethanol (2 ml) is treated with oxalic acid (0.2 g) and recrystallized from aqueous ethanol to give dioxalate (0.25 g).

mp. 197°~199° C.

Elemental Analysis (for $C_{17}H_{24}N_4O_2\cdot2(COOH)_2$): Calcd (%): C, 50.80; H, 5.68; N, 11.28. Found (%): C, 50.57; H, 5.59; N, 11.26.

EXAMPLE 90

Preparation of 3-[3-(5-methyl-1-phenyl-3-(1,2,4-triazolyl) carbonamido)propoxy]-1-dimethylaminomethylbenzene

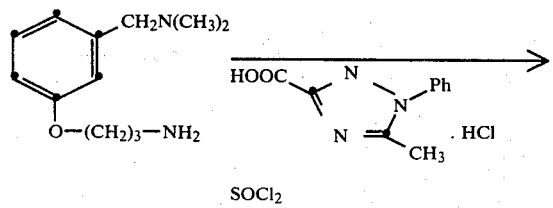

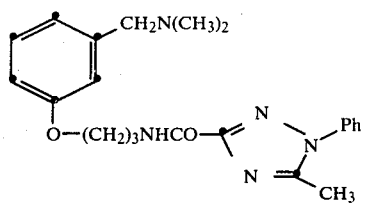

To a suspension of 5-methyl-1-phenyl-3-(1,2,4-triazolyl)carboxylic acid hydrochloride (0.82 g) and thionyl chloride (1.5 ml) in benzene (20 ml) is added dimethylformamide (0.15 ml), and the mixture is refluxed for 45 minutes and concentrated under reduced pressure. The residue is dissolved in pyridine (4 ml) and to the resulting solution is added a solution of Compound 29 (0.42 g) in pyridine (1 ml). The mixture is stirred overnight and pyridine is evaporated under reduced pressure. The residue is distributed to chloroform and aqueous sodium hydrogencarbonate. The organic layer is washed with water and then saturated brine, dried over anhydrous sodium sulfate, and concentrated. The residue is purified by chromatography (silica gel/methanol) to give Compound 33 (0.55 g) as a syrupy product.

Compound 33 is dissolved in a solution (2 ml) of 16.3% hydrochloric acid in ethanol and the solvent is evaporated under reduced pressure to give dihydrochloride.

(recrystallized from ethanol-ether)

mp. 165°~168° C.

Elemental Analysis (for $C_{22}H_{27}N_5O_2\cdot2HCl$): Calcd (%): C, 56.65; H, 6.28; N, 15.02; Cl, 15.20. Found (%): C, 56.90; H, 6.26; N, 15.02; Cl, 14.58.

EXAMPLE 91

Preparation of 3-[3-(1-cyanoiminoethyl)aminopropoxy]-1-(1-pyrrolidinylmethyl)benzene

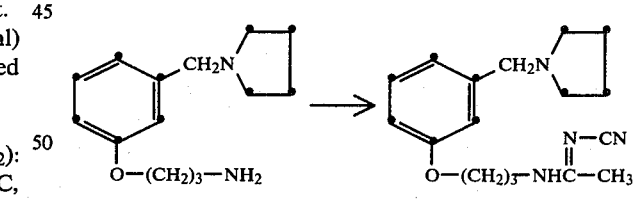

A mixture of Compound 9 (0.289 g; 1.23 mmoles), ethyl N-cyanoacetoimidate (0.276 g; 2.5 mmoles) and dry ethanol (3 ml) is stirred at room temperature for 3 days, and the solvent is evaporated. The resulting oily residue is purified by chromatography (silica gel (30 g)/methanol) to give Compound 34 (0.337 g).

Yield 91.2%

NMR: $\delta^{CDCl_3}$ 3.58s(2H, PhC$\underline{H}_2$N), 4.07t(2H, J=6 Hz, PhOC$\underline{H}_2$), 2.28s(3H, —C$\underline{H}_3$)

IR: $\nu^{film}$ 3250, 3100, 2160, 1580 cm$^{-1}$.

Monooxalate (recrystallized from ethanol-ether)

mp. 135°~137° C. (dec)

Elemental Analysis (for $C_{17}H_{24}ON_4 \cdot (COOH)_2 \cdot \frac{1}{4}H_2O$): Calcd(%): C, 57.78; H, 6.90; N, 14.18. Found(%): C, 57.58; H, 6.61; N, 13.88.

EXAMPLE 92

Preparation of 4-(3-acetamidopropoxy)-1-[2-(1-pyrrolidinyl)ethyl]benzene

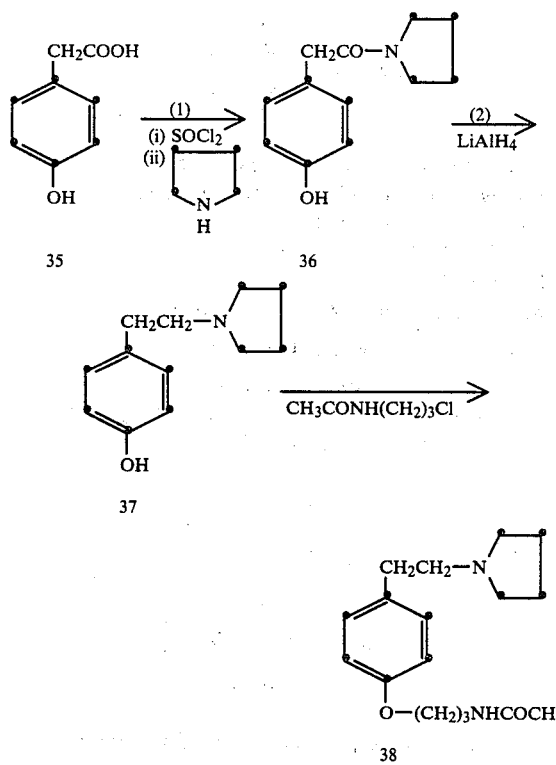

(1) A mixture of Compound 35 (4.56 g; 30 mmoles) and thionyl chloride (15 ml) is refluxed for 30 minutes and concentrated under reduced pressure. The residue is dissolved in chloroform (50 ml) and mixed with pyrrolidine (4.28 g; 60 mmoles). The mixture is stirred for 3 hours. The reaction mixture is washed with acetic acid-water and then water, dried and evaporated under reduced pressure. The residue is treated with ethanol-ether to give Compound 36 (1.7 g).

Yield: 27.6% mp. 128°~130° C.

(2) To a solution of lithium aluminium hydride (1 g; 26.7 mmoles) in dry tetrahydrofuran (20 ml) is added dropwise a solution of Compound 35 (1.5 g; 7.3 mmoles) in dry tetrahydrofuran (50 ml) at temperature below 15° C., and the resultant mixture is stirred at the same temperature for 15 minutes and at room temperature for 2 hours. While cooling, the reaction mixture is mixed with ethyl acetate (50 ml) and water (20 ml). The insoluble materials are filtered off, and the filtrate is concentrated under reduced pressure. The residue is extracted with chloroform and the extract is washed with water, dried and concentrated under reduced pressure. The oily residue is treated with ether and recrystallized from ethyl acetate to give Compound 37 (0.714 g) as crystalline product.

Yield 51.3% mp. 153°~155° C.

(3) To a suspension of sodium hydride (50% oil dispersion; 0.096 g; 2 mmoles) in dry dimethylformamide (2 ml) is dropwise added a solution of Compound 37 (0.383 g; 2 mmmoles) in dry dimethylformamide (4 ml) at 0° C. and the mixture is stirred at 0° C. for 15 minutes and at room temperature for 30 minutes. A solution of N-(3-chloropropyl)acetamide (0.537 g; 2 mmoles) in dry dimethylformamide (3 ml) is dropwise added thereto, and the resultant mixture is stirred at room temperature for 20 hours. The reaction mixture is poured into water (30 ml), extracted with water, dried, and concentrated under reduced pressure. The residue is treated with ether to give Compound 38 (0.23 g) as colorless crystals.

Yield: 39.6% mp. 89°~91° C.

NMR: $\delta^{CDCl_3}$ 2.73b(4H, C$\underline{H}_2$x2), 3.48t(2H, J=6 Hz, C$\underline{H}_2$NH), 4.07t(2H, J=6 Hz, OCH$_2$).

IR: $\nu^{Nujol}$ 3180, 1640, cm$^{-1}$.

Elemental Analysis (for $C_{17}H_{26}N_2O_2$): Calcd (%): C, 70.31; H, 9.02; N, 9.65. Found (%): C, 69.97; H, 8.98; N, 9.53.

EXAMPLE 93

Preparation of 3-[3-(4-carboxybenzamido)propoxy]-1-(1-pyrrolidinylmethyl)benzene

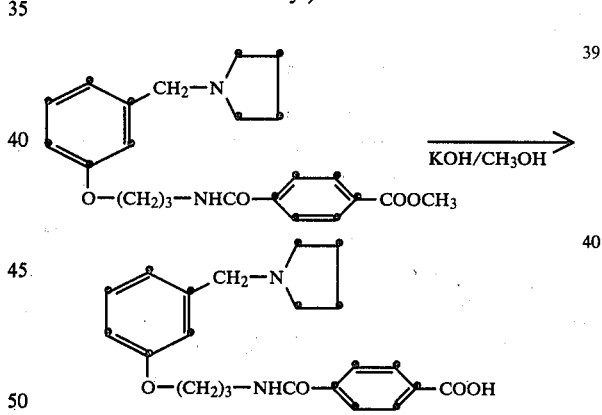

To a solution of Compound 39 (1.2 g; 3 mmoles) in methanol (20 ml) is added a solution of potassium hydroxide (0.200 g; 3.6 mmoles) in methanol (10 ml), and the mixture is refluxed under heating for 1 hour and concentrated under reduced pressure. The residue is dissolved in 99% ethanol (10 ml) and the insoluble materials are filtered off. The filtrate is treated with a solution of oxalic acid (1.5 g) in 99% ethanol (5 ml) to give monooxalate (0.781 g) as a crude product. This is recrystallized from ethanol to give the pure product (0.500 g).

mp. 166°~168° C.

Elemental Analysis (for $C_{22}H_{26}O_4N_2 \cdot (COOH)_2$): Calcd (%): C, 61.01; H, 5.97; N, 5.93. Found (%): C, 61.05; H, 6.08; N, 5.90.

EXAMPLE 94

Preparation of 3-[3-(4-carbamoylbenzamido)propoxy]-1-(1-pyrrolidinylmethyl)benzene

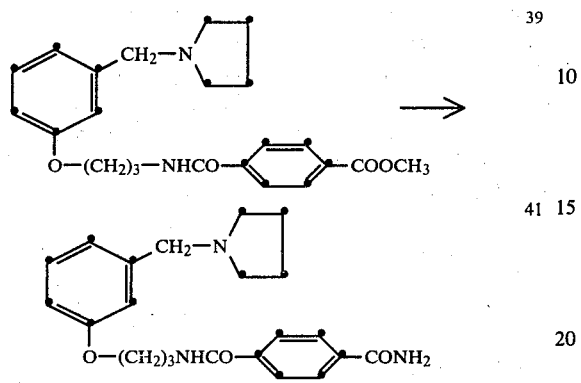

A solution of Compound 39 (1.0 g) in methanolic ammonia (ca 13%; 100 ml) is allowed to stand at room temperature for 7 days, and the mixture is concentrated under reduced pressure. The resulting residue is purified by chromatography (silica gel/methanol) to give Compound 41 (0.552 g).

Monooxalate
mp. 184°~185° C. (dec.)

Elemental Analysis (for $C_{22}H_{27}O_3N_3 \cdot (COOH_2)$: Calcd (%): C, 61.13; H, 6.20; N, 8.91. Found (%): C, 60.66; H, 6.13; N, 8.86.

EXAMPLE 95

Preparation of 3-[3-(4-methanesulfonylbenzamido)propoxy]-1-(1-pyrrolidinylmethyl)benzene

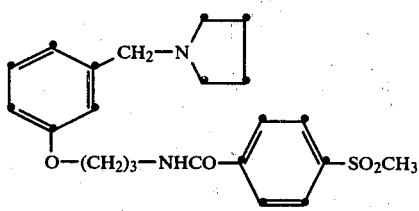

A mixture of 2,2'-dipyridyl disulfide (793 mg), triphenylphosphine (943 mg) and p-(methanesulfonyl)benzoic acid (720 mg) in dry methylene chloride(30 ml) is stirred at room temperature for 45 minutes. Compound 9 (703 mg) is added to the resulting solution, which is stirred at room temperature for 16 hours. The reaction mixture is concentrated in vacuum to give a yellow oil, which is purified on silica gel chromatography using methanol to give Compound 42 (891 mg) in 71.3% yield.

NMR: $\delta^{CDCl_3}$ 3.60s(2H), 3.03s(3H).
mp. 135°~136° C.
Tartarate.½H₂O, mp. 116°~118° C.
Monoxalate, mp. 172°~173° C. (dec.)

EXAMPLE 96

Preparation of 3-[3-(4-methanesulfonyl-3-nitrobenzamido)propoxy]-1-(1-pyrrolidinylmethyl)benzene

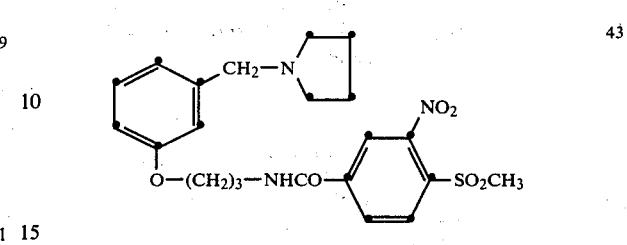

Compound 43 is prepared as an oil from Compound 9 and 4-methanesulfonyl-3-nitrobenzoic acid in the same manner as in Example 95.

NMR: $\delta^{CDCl_3}$ 4.15t(2H, J=6 Hz), 3.58s(2H), 3.37s(3H).

Monoxalate, mp. 179°-181° C. (dec.)

EXAMPLE 97

Preparation of 3-[3-(4-methanesulfonamidobenzamido)propoxy]-1-(1-pyrrolidinylmethyl)benzene

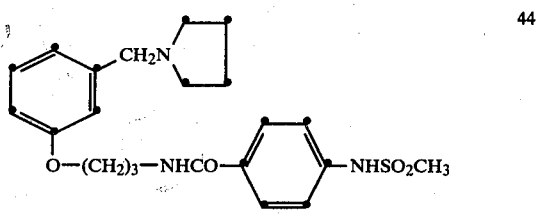

Compound 44 is prepared from Compound 9 and p-(methanesulfonamido)benzoic acid in the same manner as in Example 95.

NMR: $\delta^{CDCl_3}$ 4.12t(2H,J=6 Hz,OCH₂), 3.63s(2H,ArC$\underline{H_2}$N), 3.02s(3H,CH₃).
mp. 133°~134° C.

EXAMPLE 98

| Formulation of Tablet: | |
|---|---|
| 3-(3-Acetamidopropoxy)-1-(1-pyrrolidinylmethyl)-benzene oxalate | 50 mg |
| Wheat starch | 85 mg |
| Lactose | 160 mg |
| Magnesium stearate | 5 mg |
| | 300 mg |

What we claim is:
1. A compound of the formula:

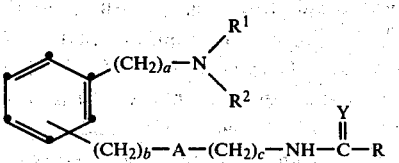

wherein
A is oxygen or sulfur,

Y is oxo or thioxo,
a is an integer of 1 to 3,
b is an integer of 0 to 3,
c is an integer of 1 to 4,
$R^1$ is $C_1$ to $C_5$ alkyl,
$R^2$ is hydrogen or $C_1$ to $C_5$ alkyl, or
$R^1$ and $R^2$ taken together represent pyrrolidinyl, and
R is pyridyl or pyridyl substituted by 1 to 3 substituents selected from the group consisting of halogen, nitro, oxo, phenyl, $C_1$ to $C_5$ alkyl and $C_1$ to $C_5$ alkanoyl or a pharmaceutically acceptable acid addition salt thereof.

2. A compound according to claim 1, namely 3-[(2-nicotinamidoethyl)thiomethyl]-1-(dimethylaminomethyl)benzene.

3. A compound according to claim 1, namely 3-(3-isonicotinamidopropoxy)-1-(1-pyrrolidinylmethyl)benzene.

4. A compound according to claim 1, namely 3-(3-nicotinamidopropoxy)-1-(1-pyrrolidinylmethyl)benzene.

5. A compound according to claim 1, namely 3-(3-picolinamidopropoxy)-1-(1-pyrrolidinylmethyl)benzene.

6. A pharmaceutical composition for use in the treatment of patients suffering from peptic ulcer which comprises a pharmaceutically effective amount of the compound of claim 1 and an inert pharmaceutical carrier or diluent thereof.

7. A method for the treatment of peptic ulcer which comprises administering a pharmaceutical composition of claim 6 to a patient suffering from peptic ulcer.

* * * * *